Figure 1:
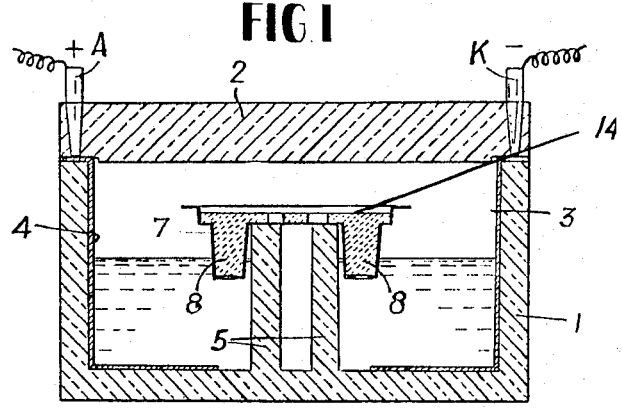

United States Patent [19]

Eibl et al.

[11] 3,951,776

[45] Apr. 20, 1976

[54] LOW-VOLTAGE CROSS MIGRATION ELECTROPHORESIS APPARATUS

[75] Inventors: Johann Eibl; Ewald Molinari; Gerald Eder, all of Vienna, Austria

[73] Assignee: Medizinische Produkte Immuno Aktiengesellschaft fur Chemish, Austria

[22] Filed: Feb. 13, 1974

[21] Appl. No.: 442,158

Related U.S. Application Data

[63] Continuation-in-part of Ser. No. 296,864, Oct. 12, 1972, abandoned.

[30] Foreign Application Priority Data

Oct. 15, 1971 Austria .............................. 8943/71
July 21, 1972 Austria .............................. 6296/72

[52] U.S. Cl. .......................... 204/299 R; 23/230 B; 230/230 R; 204/180 G
[51] Int. Cl.[2] ..................... B01K 5/00; G01N 31/00
[58] Field of Search .................... 204/180 G, 299; 252/182, 408; 23/230 B, 230 R

[56] References Cited
UNITED STATES PATENTS 3,674,678  7/1972  Post, Jr. et al. ..................... 204/299
3,773,646  11/1973  Mandle et al. ..................... 204/299

OTHER PUBLICATIONS

Näntö et al., "Optimal Cond. in Starch–Gel Elecphor. of Heat Denatured Collagen," Jrnl. Amer. Leather Chemists Assoc., Vol. LX, No. 2, Feb., 1965, pp. 63–71.

Primary Examiner—G. L. Kaplan
Assistant Examiner—A. C. Prescott
Attorney, Agent, or Firm—Steinberg & Blake

[57] ABSTRACT

A low-voltage apparatus for demonstrating antigens in body liquids by cross-migration electrophoresis. The apparatus comprises a container filled with a buffer solution, which container has an anode and a cathode chamber and houses a gel-carrying tray. Recesses for receiving antigens and antibodies are provided in the gel and arranged to lie opposite each other in pairs at a distance of between 2 and 5 mm. The gel has a horizontal heat-exchange surface area of at least 50 cm². The gel layer reaction zone between the recesses is between 0.5 and 1.5 mm thick and has a cross-sectional area of between 100 and 150 mm². The apparatus permits a current passage of 100 milliampere, resulting in a current density of 0.7 milliampere/mm² in the gel layer reaction zone.

8 Claims, 4 Drawing Figures

U.S. Patent   April 20, 1976   3,951,776

LOW-VOLTAGE CROSS MIGRATION ELECTROPHORESIS APPARATUS

This application is a continuation-in-part of our co-pending application Ser. No. 296,864, filed Oct. 12, 1972, now abandoned.

The invention relates to a low-voltage cross-migration electrophoresis apparatus for demonstrating antigens in body liquids, comprising a buffer solution receiving container divided in longitudinal direction by a separating dam into an anode and a cathode region interspersed with electrodes, and a tray covering the separating dam and accommodating a gel layer, recesses for receiving the antigen to be investigated and the antibodies being provided in the gel, which recesses are arranged to lie opposite each other.

The term "cross-migration electrophoresis" defines an electrophoresis in which antigens and antibodies migrate towards each other under the influence of an electric field.

In 1964 Blumberg et al. (JAMA 1965, 191, 541) discovered a new antigen, the Australia serum-hepatitis/hepatitis associated antigen (AU/SH/HAA) in the course of immune genetic studies by means of the so-called Ouchterlony method. The AU/SH/HAA proved to be the agent of the homologue serum hepatitis which may be communicated parenterally and possibly also perorally. In blood transfusions AU/SH/HA antigen containing blood leads, in a high degree to icteric and anicteric forms of serum hepatitis in the recipients of such blood. Also, it can be demonstrated in various autoimmune diseases.

The demonstration of AU/SH/HA antigens seems to be of importance in many medical examinations, i.e. in the examination of blood and plasm donors (blood preserves and plasm derivates); in the early diagnosis of the prodromal stage of serum hepatitis; in the distinction between serum hepatitis and infectious (epidemic) hepatitis, in particular in the first days of the acute phase; in the decision whether chronical liver diseases and various autoimmune diseases are related to homologue serum hepatitis and in the discovery of possible virus carriers of the homologue serum hepatitis (hospital and laboratory personnel).

There are numerous fields where such investigations may be carried out, such as blood banks, plasm phoresis stations and related organisations, medical diagnostic laboratories, gastroenterological divisions, hemodialysis stations, intensive care stations and infectious stations.

For determining the AU/SH/HA antigen, Grabar and Williams developed the so-called technology of immune electrophoresis, which refers to an electrophoresis of a protein mixture in a buffered agargel followed by a two-dimensional immune diffusion of the separated components towards an immune serum applied in parallel to the separation direction. At the areas of contact of antigen (AG) and antibody (AK) a precipitation line occurs in the agar.

In order to increase the sensitivity of the method and in order to shorten the time necessary for it, the so-called cross-migration electrophoresis or electrosyneresis is applied. In this operation method a precipitation line is created owing to the fact that the AG and the AK have different migration speeds. In demonstrating AU/SH/HAA it is necessary that the AG migrates to the anode and the AK as immune globulin moves by electroendosmosis to the cathode. Principally, all combinations of qualitative and quantitative electrophoresis are possible with the immune electrophoresis.

In the known, customary electrophoresis twin rows of recesses or holes lying opposite each other are provided in a gel plate for receiving the antigen and the antibodies to be investigated. The voltages which were necessary for operating the electrophoresis apparatus sometimes amounted to as much as 1000 V when using an object holder with a length of 76 mm, they amounted still to 200 V; with conventional electrophoresis apparatus it took an average period of 45 to 90 minutes until positive reactions occured and were terminated.

Another type of the known electrophoretic apparatus has its electrodes embedded within the gel; although such known apparatus may be operated at low voltages, the current densities must be kept low and the reaction takes considerable time, as otherwise the gel surrounding the electrodes would melt and consequently the supply of current would be interrupted, since heat cannot be abducted.

It is an object of the present invention to avoid the above described disadvantages and difficulties by providing a cross-migration electrophoresis apparatus that can be operated at low voltages and at the same time achieves a high current density for speeding up the migration and, thus, the reaction of antigen and antibodies while preventing melting off and drying out of the gel. It is, thus, a further object of the invention to provide for a relatively large horizontal surface area of the gel so as to enable a sufficient abduction of heat without additional cooling. Still further objects of the invention are to minimize the migration path of antigens and antibodies, to minimize the time required for the occurence and termination of reactions and to enable a higher sensitivity of indication. A further object of the invention is to avoid erroneous results that formerly occured owing to overheating, and to increase safety in operation by prevention of accidents, in particular to safeguard handling of the apparatus without danger, even if conductive parts are touched.

These objects of the invention are achieved with a low-voltage cross-migration electrophoresis apparatus for demonstrating antigens in body liquids which apparatus comprises, in combination, a buffer solution receiving container adapted to be closed by a cover, a separating dam dividing said container in longitudinal direction into an anode chamber and a cathode chamber, electrodes positioned and fixed in said anode chamber and cathode chamber, a tray arranged on said separating dam and connecting the anode chamber with the cathode chamber, a gel layer positioned in said tray and accomodating a current migration path, said gel layer having a horizontal heat-exchange surface area of at least 50 cm$^2$, two rows of recesses for receiving the antigens to be demonstrated and antibodies, the recesses being arranged in pairs in the gel layer to lie opposite each other at a distance of between 2 and 5 mm, preferably at a distance of not more than 2.5 mm, and enframing a gel layer reaction zone having a thickness of between 0.5 and 1.5 mm and a cross-sectional area of between 100 and 150 mm$^2$, the apparatus, in operation, permitting a current passage of 100 milliampere resulting in a current density of 0.7 milliampere/mm$^2$ in the gel layer reaction zone, which enables a reaction of the antigens and the antibodies within a minimum of 15 and a maximum of 30 minutes without melting or drying of the gel layer.

According to an advantageous embodiment of the invention a tray in the form of a substantially U-shaped stencil having limbs that extend downwardly into the buffer solution is employed. The gel is cast into that U-shaped stencil, thus forming a substantially U-shaped gel layer. In this embodiment the current migration path in the gel layer amounts to between 35 and 40 mm, preferably to not more than 35 mm. The stencil which immerses into the buffer solution and delimits the limbs of the U-shaped gel layer at the outside and inside is preferably open at its underside. Advantageously the stencil may be provided with bottom-contact-holes which are in the same vertical plane and thus in alignment with the recesses in the gel layer destined for receiving antigen and antibodies and arranged to lie opposite each other in pairs. In this embodiment the bottom-contact-holes effect focussing of the current whereby the speed and sensitivity of indication are further increased.

The buffer solution receiving container and the tray that carries the gel can be made of polypropylene, so that they can readily be heat-sterilized, e.g. in an autoclave, so that they may be used repeatedly.

The buffer solution that may advantageously be employed in the apparatus of the present invention comprises 5,5 diethyl-barbituric acid sodium salt, sodium acetate and citric acid.

In accordance with a particularly preferred embodiment of the invention a disposable cross-migration electrophoresis apparatus is provided, the preferably rectangular, container of which is made of a cheap plastics material e.g. of polyvinylchloride, and in which electrodes of non-precious metal, preferably of aluminum, are employed. These electrodes may be welded onto the inner wall of the electrophoresis chamber. When electrodes of non-precious metal, particularly of aluminum, are employed it is essential that the buffer solution contains a reducing agent, preferably sodium sulfite, which dissolves oxide layers that form on the electrodes. Such disposable apparatus is intended for one single use and, thus, avoids any danger of infection, particularly of serum hepatitis.

As already mentioned, the use of a specific buffer solution is another aspect of the invention. A preferred composition of the buffer solution is the following:

| | |
|---|---|
| 5,5 diethyl-barbituric acid sodium salt | 8.15 g |
| sodium aceticum × 3 H$_2$O | 10.70 g |
| citric acid × 1 H$_2$O | 1.11 g |
| sodium sulfite | 10.00 g |
| aqua dest. | 1000 ml. |

Figure 2:
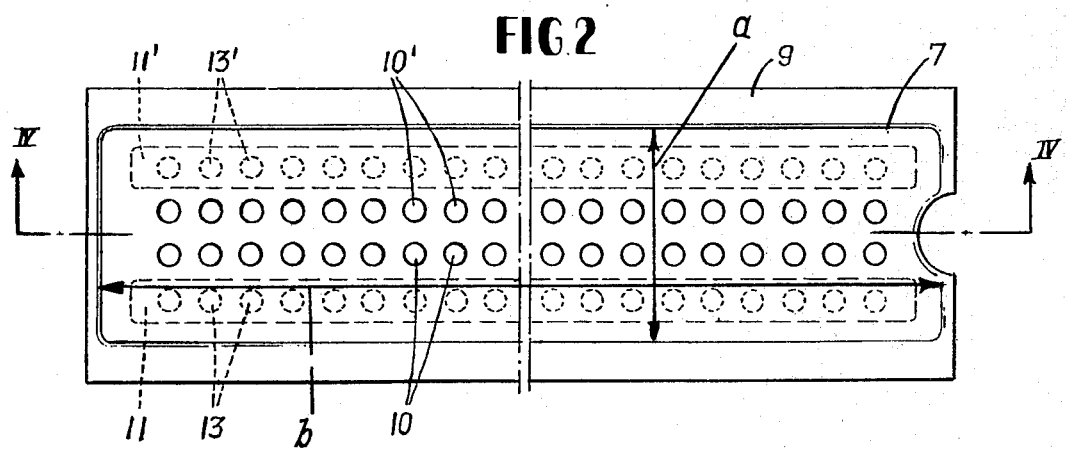
Figure 3:
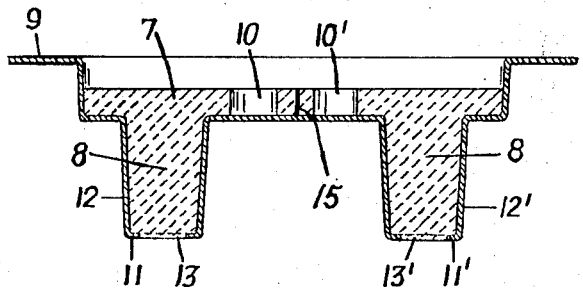
Figure 4:
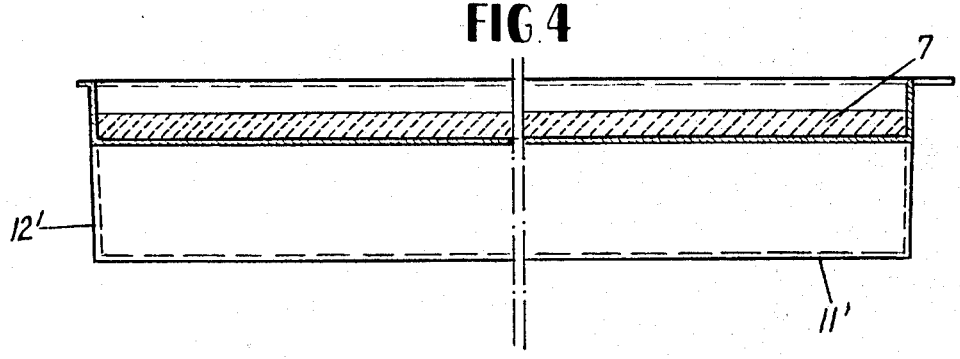

In order that the apparatus of the invention may be more fully understood, an embodiment thereof shall now be described with reference to the accompanying drawings, in which FIG. 1 is a vertical sectional view of the apparatus,
FIG. 2 is a top view,
FIG. 3 is a vertical sectional view of a stencil with a gel layer therein,
FIG. 4 is a sectional view of the stencil (gel layer carrying tray) along the line IV—IV in FIG. 2.

The apparatus comprises a rectangular tank 1 which is suitably made of polyvinylchloride and may be covered by a cover 2. Through bores in the cover 2 cathode K and anode A are inserted which, in the form of aluminium sheets 3 and 4, continue in the interior of the tank along the side walls and along part of the bottom. The electrode sheets, thus, have an angular cross-section. Fillets 5 extend in upward direction from the bottom of the tank; they constitute a separating dam and divide the tank 1 in longitudinal direction into the cathode and the anode region. The separating dam with the fillets 5 supports a tray carrying the gel layer 7 which thus bridges the separating dam and immerses into the buffer solution with its downwardly extending limbs 8. As may be derived from FIG. 3, the gel layer is cast into a substantially U-shaped stencil 9. The stencil is likewise suitably made of a synthetic material. In the gel layer the recesses or holes 10,10' are arranged to lie opposite each other in pairs at a distance of not more than 5 mm, preferably not more than 2.5 mm. As may be derived from FIGS. 2 and 3, holes 13,13' are provided in the bottoms 11,11' of the trough-shaped parts 12,12' of the stencil immersing into the buffer solution. The holes 13,13' are in the same vertical plane as and thus in alignment with the holes 10,10' destined for receiving the antigen and antibodies. All four holes thus lie in one row. This arrangement offers the great advantage that owing to the provision of the bottom-contact-holes the current is focussed so that the electrophoresis is accelerated. The surface 14 indicated in FIG. 1, having a width $a$ and a length $b$, as shown in FIG. 2, constitutes a horizontal heat-exchange surface area, which, in accordance with the invention, must amount to at least 50 cm$^2$, so as to sufficiently abduct the heat developing during the passage of current. In the present example the layer thickness at the line 15, indicated in FIG. 3, amounts to 1 mm and, with a length $b$ of 140 mm, the cross-sectional area is 140 mm$^2$. This cross-sectional area, which, as it has been pointed out above, must lie within the range of 100 and 150 mm$^2$, is essential.

The functioning of the apparatus of the invention will now be illustrated by the following Examples.

EXAMPLE 1

The above described apparatus was used for determining the AU/SH/HA-antigen in human serum by cross-migration electrophoresis in an agar medium. This was performed by pipetting the anti-AU/SH/HA-serum into the row of recesses on the anode side, while the sera to be investigated in respect of AU/SH/HA-antigen were pipetted into the row of recesses on the cathode side. Thereupon the above described 5,5 diethyl-barbituric acid sodium salt buffer solution was filled into the anode and cathode chamber and the tray was inserted into the tank. Upon closing of the tank the electrophoresis was started, applying a current passage of 100 milliampere, which resulted in a current density of 0.7 milliampere/mm$^2$ in the reaction zone. After a 30-minute electrophoresis a precipitation line could be recognized between the opposite recesses in the case of a positive reaction.

EXAMPLE 2

The same apparatus was used under the same conditions as outlined in Example 1 for determining the $\alpha_1$-fetoprotein by carrying out an electrophoresis in an agar medium. This was done by pipetting the anti-$\alpha_1$-fetoprotein serum into the row of recesses on the anode side, while the sera to be investigated were pipetted into the row of recesses on the cathode side. After a 30-minute duration of the electrophoresis a precipitation line could be recognized between the opposite recesses in the case of a positive reaction.

What we claim is:

1. A disposable low-voltage cross-migration electrophoresis apparatus for demonstrating antigens in body liquids, comprising, a rectangular container made of plastics material and containing a buffer solution including a reducing agent, which container is adapted to be closed by a cover, a separating dam dividing said container in longitudinal direction into an anode chamber and a cathode chamber, electrodes made of non-precious metal, oxide layers forming thereon being dissolved by the reducing agent included in the buffer solution, which electrodes are positioned and fixed in said anode chamber and cathode chamber, a tray arranged on said separating dam and connecting the anode chamber with the cathode chamber, a gel layer positioned in said tray and accommodating a current migration path, said gel layer having a horizontal heat-exchange surface area of at least 50 cm$^2$, two rows of recesses for receiving the antigens to be demonstrated and antibodies, the recesses being arranged in pairs in the gel layer to lie opposite each other at a distance of not more than 2.5 mm and enframing a gel layer reaction zone having a thickness of between 0.5 and 1.5 mm and a cross-sectional area of between 100 and 150 mm$^2$, for permitting a current passage of 100 milliampere, resulting in a current density 0.7 milliampere/mm$^2$ therethrough, whereby a reaction of the antigens and the antibodies occurs within a minimum of 15 and a maximum of 30 minutes without melting or drying of the gel layer.

2. A disposable low-voltage cross-migration electrophoresis apparatus for demonstrating antigens in body liquids, comprising, a rectangular container made of a plastics material and containing a buffer solution comprising 5.5 diethyl-barbituric acid sodium salt, sodium acetate, citric acid and a reducing agent, which container is adapted to be closed by a cover, a separating dam dividing said container in longitudinal direction into an anode chamber and a cathode chamber, electrodes made of aluminum, oxide layers forming thereon being dissolved by the composition of the buffer solution, which electrodes are positioned and fixed in said anode chamber and cathode chamber, a substantially U-shaped stencil arranged on said separating dam and connecting the anode chamber with the cathode chamber, said stencil having limbs downwardly extending into the buffer solution, a substantially U-shaped gel layer in said U-shaped stencil accommodating a current migration path of between 35 and 40 mm, said gel layer having a horizontal heat-exchange surface area of at least 50 cm$^2$, two rows of recesses for receiving the antigens to be demonstrated and antibodies, the recesses being arranged in pairs in the gel layer to lie opposite each other at a distance of not more than 2.5 mm and enframing a gel layer reaction zone having a thickness of between 0.5 and 1.5 mm and a cross-sectional area of between 100 and 150 mm$^2$, bottom-contact holes in the substantially U-shaped stencil lying in the same vertical plane as the recesses for receiving the antigens to be demonstrated and the antibodies, for permitting a current passage of 100 milliampere, resulting in a current density of 0.7 milliampere/mm$^2$ therethrough, whereby a reaction of the antigens and the antibodies occurs within a minimum of 15 and a maximum of 30 minutes without melting or drying of the gel layer.

3. A buffer solution to be used in a container of a low-voltage cross-migration electrophoresis apparatus for demonstrating antigens in body liquids, comprising 5,5 diethyl-barbituric acid sodium salt, sodium acetate and citric acid.

4. The buffer solution set forth in claim 3, wherein, in addition, a reducing agent is contained.

5. The buffer solution set forth in claim 4, wherein said reducing agent is sodium sulfite.

6. A low-voltage cross-migration electrophoresis apparatus for demonstrating antigens in body liquids, comprising a plastic container and a buffer solution situated therein and including a reducing agent, said container being adapted to be closed by a cover, a separating dam dividing said container into an anode chamber and a cathode chamber, electrodes positioned and fixed in said anode chamber and cathode chamber, with oxide layers which form thereon becoming dissolved by the reducing agent included in the buffer solution, a tray situation on said separating dam and connecting the anode chamber with the cathode chamber, a gel layer positioned in said tray and accommodating a current migration path, said gel layer having a horizontal heat-exchange surface of a predetermined area, two rows of recesses for receiving the antigens to be demonstrated and antibodies, said recesses being arranged in pairs in said gel layer at a given distance opposite each other and enframing a gel layer reaction zone of a given thickness and cross-sectional area for permitting passage of a given current resulting in a given current density for achieving a reaction of the antigens and the antibodies within a given time without melting or drying of the gel layer.

7. The combination of claim 6 and wherein said recesses are situated opposite each other at a distance of between 2 and 5 mm.

8. The combination of claim 6 and wherein said electrodes are made of a non-precious metal.

* * * * *

UNITED STATES PATENT AND TRADEMARK OFFICE
CERTIFICATE OF CORRECTION

PATENT NO. : 3,951,776
DATED : April 20, 1976
INVENTOR(S) : Johann Eibl; Ewald Molinari, Gerald Eder It is certified that error appears in the above-identified patent and that said Letters Patent are hereby corrected as shown below:

In the heading, item [73], the name of the assignee should be:
--Immuno Aktiengesellschaft fur chemisch-medizinische Produkte--.

Column 6, line 40, "situation" should read --situated--.

Signed and Sealed this

Twenty-ninth Day of March 1977

[SEAL]

Attest:

RUTH C. MASON
*Attesting Officer*

C. MARSHALL DANN
*Commissioner of Patents and Trademarks*